United States Patent [19]

Levine et al.

[11] Patent Number: 4,779,976

[45] Date of Patent: Oct. 25, 1988

[54] MULTIPARAMETER HEMATOLOGY MEASUREMENT FOR VETERINARIANS

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 91,380

[22] Filed: Aug. 31, 1987

[51] Int. Cl.$^4$ ............................................. G01N 33/16
[52] U.S. Cl. ..................................................... 356/39
[58] Field of Search ............... 356/39; 73/53, 57, 149, 73/64.1

[56] References Cited

U.S. PATENT DOCUMENTS

| | | | |
|---|---|---|---|
| 3,617,222 | 11/1971 | Matte | 356/39 X |
| 3,861,800 | 1/1975 | Rapoza et al. | 356/39 |
| 4,071,891 | 1/1978 | Barrows | 356/39 X |
| 4,148,607 | 4/1979 | Bernoco et al. | 356/39 X |
| 4,156,570 | 5/1979 | Wardlaw | 356/39 X |
| 4,190,328 | 2/1980 | Levine et al. | 356/246 X |

*Primary Examiner*—Richard A. Rosenberger
*Attorney, Agent, or Firm*—William W. Jones

[57] ABSTRACT

Blood samples of animals are taken and analyzed for several different cell parameters. The analysis is made by centrifuging an anticoagulated blood sample in a capillary tube containing a float which physically elongates certain of the component cell layers in the sample. The instrument in which the parameter measurements are made is computerized and can be preset to take measurements of the blood of any one of several different types of animals whose respective blood cells have different packing coefficients.

3 Claims, 1 Drawing Sheet

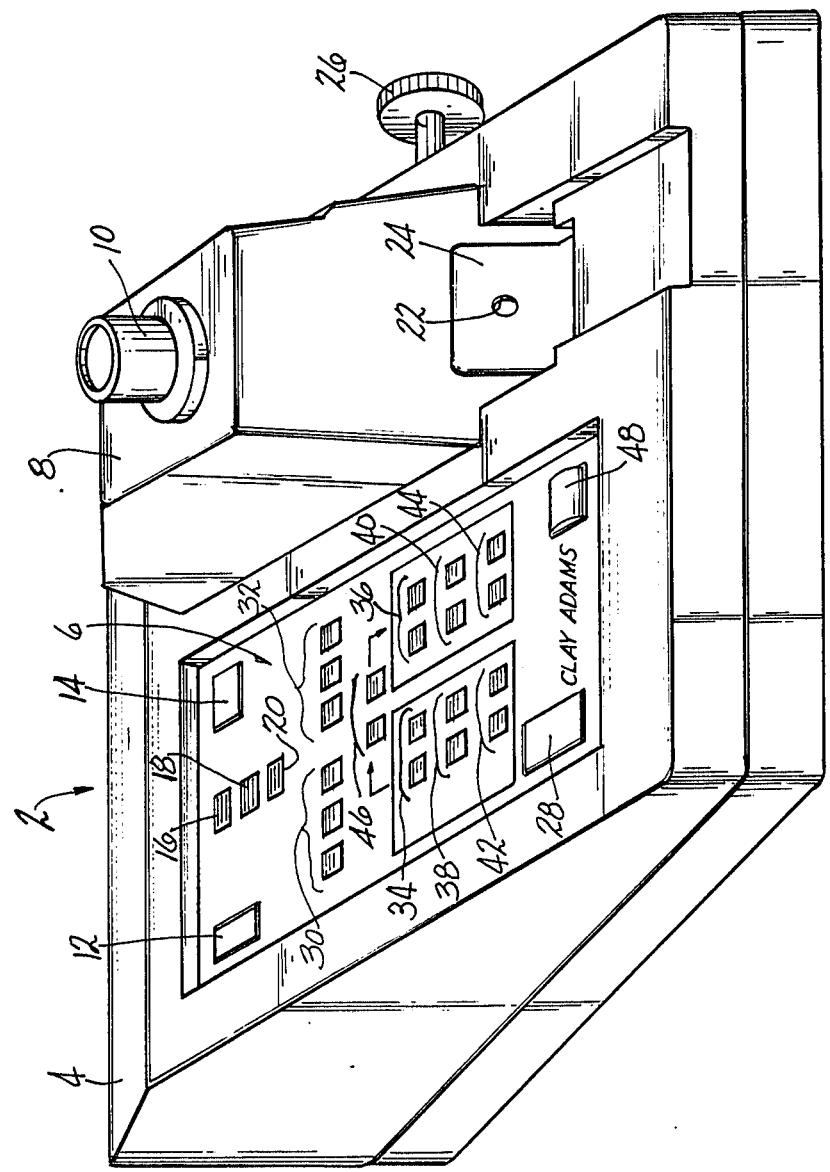

MULTIPARAMETER HEMATOLOGY MEASUREMENT FOR VETERINARIANS

This invention relates to a method and instrument for use by veterinarians in measuring blood cell counts of a number of different types of animals. More particularly, this invention relates to an instrument which can measure bood cell counts of different animals by simply identifying the types of animal blood being tested before the results of the testing are displayed.

A technique has been developed for measuring blood cell counts by drawing anticoagulated blood into a capillary tube which has a cylindrical float in the tube. The blood samples is then centrifuged in the capillary tube so that the blood cells will layer out according to their specific gravity. The float, being located in the area of the cells that one desires to measure, will elongate certain of the layers of cells so as to physically magnify the elongated cell layers. The cell counts are made in an instrument which measures the axial length of the various cell layers, enters the measured lengths into a computer control which, in turn, converts the measured lengths into cell counts, relying on cell packing coefficient data previously inputted into the computer control. This technology is disclosed in U.S. Pat. Nos. 4,027,660, granted June 7, 1977 to S. C. Wardlaw et al; 4,077,396, granted Mar. 7, 1978 to S. C. Wardlaw et al; 4,082,085, granted Apr. 4, 1978 to S. C. Wardlaw et al; 4,137,755, granted Feb. 6, 1979 to S. C. Wardlaw et al; 4,156,570 granted May 29, 1979 to S. C. Wardlaw et al; 4,209,226, granted June 24, 1980 to S. C. Wardlaw et al; 4,558,947, granted Dec. 7, 1985 to S. C. Wardlaw, and others. This technique has proven to be immensely successful for use in the analysis of human blood.

The aforesaid technique has been modified for use in connection with veterinarian sciences so as to be useful in the dectection of heartworm micro filaria, as disclosed in U.S. Pat. No. 4,190,328, granted Feb. 26, 1980 to Robert A. Levine et al, but its applicability to general blood count testing in animals has been restricted. The reason for the wide acceptance in the medical profession but narrow applicability in the veterinarian field is because the blood cell packing coefficient characteristics of patients seen by physicians are all substantially the same because patients are all human beings, whle in veterinarian practice the patients commonly seen by a veterinarian, i.e. dogs, cats, horses, or other animals will have different blood cell packing coefficient characteristics, depending on which species of animal blood is being examined. Since the average veterinarian practice is not limited to any one species of animal, up to the conception of our invention, the aforesaid technology has not been widely used by the veterinarian field.

Our invention constitutes an improvement of the aforesaid blood count measuring technology which adopts said technology to broad use in the veterinarian field. Our invention contemplates an instrument and method which is controlled by a microprocessor and which is capable of determining blood cell counts of animals which have different blood cell characteristics, such as dogs, cats, horses, cows, or the like. We purpose the use of a single instrument which is controlled by a microprocessor which is capable of measuring blood cell layers in centrifuged blood samples and which can be manually set to correctly select pre-inputted cell size information pertaining to the animal in question. The micrprocessor then converts the cell layer measurements to cell count data which pertains to the animal in question. The instrument that we propose will include a microprocessor which has a plurality of inputted programs which are each specific to a different animal species. For example, the instrument can be used to determine blood cell counts of different animals, such as dogs, cats and horses. The blood sample will be centrifuged into its constituent cell layers and then placed in the instrument. The instrument will have a selector button so that the operator can select the proper animal. The lengths of the blood cell layers are measured and the proper animal identification is entered into the instrument. When the proper animal is identified for the instrument, the microprocessor selects the pre-inputted program that has the proper cell packing characteristics for the animal in question. The microprocessor than converts the various blood cell layer lengths into cell count information in accordance with the program for the animal in question.

It is therefore an object of this invention to provide a blood sample analyzer which can perform blood cell counts on blood taken from a member of different animal species.

It is a further object of this invention to provide a blood sample analyzer of the character described wherein the blood samples are analyzed in a centrifuged capillary tube.

It is an additional object of this invention to provide a blood sample analyzer of the character described which includes a microprocessor control which is inputted with pertinent cell size and cell packing data specific to several different animal species.

It is another object of this invention to provide a blood sample analyzer of the character described wherein the operator selects the appropriate animal species from a plurality thereof available, thus enabling use of the proper cell size and cell packing program in the microprocessor to calculate the appropriate cell count data.

These and other objects and advantages of the invention will become more readily apparent from the following detailed description of a preferred embodiment of the invention when taken in conjunction with the accompanying drawing which is a perspective view of the instrument in question.

The instrument, denoted generally by the numeral 2, includes a casing 4 in which the lighting, optics, spinning motor and microprocessor are housed. The internal components in the casing 2 operate generally as described in U.S. Pat. No. 4,156,570 granted May 29, 1979 to S. C. Wardlaw, which is specifically incorporated herein in is entirety by reference. The measurement of the cell band lengths can also be made according to the disclosure of U.S. Pat. No. 4,558,947, granted Dec. 17, 1985 to S. C. Wardlaw, which is also incorporated herein in its entirety by reference. The instrument includes a panel 6 adjacent to a housing 8 for the cell-viewing ocular piece 10. The panel 6 presents the various control buttons and indicia display windows. On the control panel there is disposed an on-off push button 12 which energizes the electrical components in the instrument. The button 12 is a rear lit button which, when lit, indicates that the instrument is "on". The button 14 is a "select" button which is used to identify the animal species whose blood is being sampled. The instrument 2 has, for example, three different LED windows 16, 18 and 20 which are controlled by the select button 14. The windows 16, 18 and 20 have associated indicia which correspond to the different animal species which the veterinarian treats. For example, the instrument 2 can be specific to canines (C); felines (F), and equines (E). The technician, knowing the type of animal whose blood is being tested utilizes the select button to illuminate the LED window which corresponds to the animal being tested. This step can be performed either before or after the cell band length measurements are made, but before the resulting cell count information is displayed on the instrument.

After the blood sample has been centrifuged, the capillary tube containing the centrifuged blood sample is inserted into an opening 22 in the instrument which communicates with a tube holder 24 which is axially movable per the aforereferenced U.S. Pat. No. 4,156,570, and the U.S. Pat. No. 4,558,947. A knob 26 allows the technician to move the holder 24 to make the appropriate measurements. After the instrument is turned on, and after each cell layer is measured, the button 28 is pressed to enter the cell band measurement into the computer's memory. Measurements will be made successively from one end of the tube to the other, beginning either with the red cells, or platelets, depending on how the computer is programmed, which will, of course, be identified for the technician by instructions on how the instrument operates. After all of the measurements have been made and entered, the cell count information will be displayed on the sereral LED banks on the instrument. The LED bank 30 will display the hematocrit count of the sample; the bank 32 will display the platelet count of the sample; the bank 34 will display the absolute eosinophil count, while the bank 36 will display an eosinophil count as a percent of the total white blood cell count. The bank 38 will display the total granulocyte count and the bank 40 will display the granuloclyte count as a percentage of the total white blood cell count. The bank 42 will display the total lymphocyte/monocyte count and the bank 44 will display the lymphocyte/monocyte count as a percentage of the total white blood cell count. The bank 46 displays the total white blood cell count. After all of the various cells counts are recorded in the animal's medical report, the button 48 is pressed to clear the instrument thereby preparing for the next reading. The entire aforesaid procedure can easily be accomplished in one minute or less.

Regarding the eosinophil measuring capabilities of the instrument of this invention, prior hereto there was no quick and accurate way of measuring eosinophil counts in the blood of animals. Eosinophils are blood cells which are present in the centrifuged blood sample at the top of the granulocyte layer, and which form a distinctly colored orange-brown band which is readily detectable. The eosinophil population is frequently elevated in animals that are infected with intestinal parasites or affected by allergic disorders such as eczema or asthema.

It will be readily appreciated that the instrument of the invention is capable of reading blood cell counts of the blood of more than one type of animal. The instrument can be tailored for any particular veterinarian practice in that an animal's blood cell characteristics can be inputted into the microprocessor in the instrument. Additionally, for the first time, the instrument can perform a quick quantitative analysis of the eosinophil cell population in the animal's blood which population is indicative of parasitic infestation or allergenic disorders in the animal.

Since many changes and variations of the disclosed embodiment of this invention may be made without departing from the inventive concept, it is not intended to limit this invention otherwise than as required by the appended claims.

What is claimed is:

1. An instrument for measuring blood cell counts from the blood of a plurality of different animal species, said instrument comprising:
   (a) a housing;
   (b) means for holding a transparent capillary tube containing a centrifuged sample of blood in said housing;
   (c) means on said housing for recognizing cell band interfaces in the centrifuged sample of blood;
   (d) means for moving the capillary tube along its axis with respect to said interfaces to measure axial cell band lengths;
   (e) microprocessor means in said housing for receiving said band length data and for converting cell band length data into cell count information, said microprocessor means having separately inputted therein, blood packing characteristics of several different blood cell types for more than one species of animal;
   (f) indicator means in said housing for selecting a particular animal species from a plurality of available different animal species which corresponds to the several species whose blood cell type characteristics are inputted in said microprocessor means, said means for selecting being operable to provide an indication of the species selected, and also being operable to enable said microprocessor means to utilize only the inputted cell packing characteristics for the selected species to determine the cell count information from the cell blood length data; and
   (g) display means for providing numerical indications of the cell count information for the different blood cell types of the selected species of animal.

2. The instrument of claim 1 wherein said microprocessor means contains inputted information relating to eosinophil cells found in different animal species.

3. An instrument for use for quantifying eosinophil cell counts in blood samples taken from a plurality of different animal species said instrument comprising:
   (a) a housing;
   (b) means for holding a transparent capillary tube containing a centrifuged sample of blood in said housing;
   (c) means on said housing for recognizing the eosinophil cell band interfaces in the centrifuged sample of blood;
   (d) means for moving the capillary tube along its axis with respect to said interfaces to measure axially the eosinophil cell band length;
   (e) microprocessor means in said housing for receiving cell band length data and for converting cell band length data into cell count information, said microprocessors means having separately inputted therein blood packing characteristics of eosinophil cell types for more than one species of animal;
   (f) indicator means in said housing or selecting a particular animal species from a plurality of available different animal species which correspond to the several species whose eosinophil cell type characteristics are inputted in said microprocessor means, said means for selecting being operable to provide an indication of the species selected, and also being operable to enable said microprocessor means to utilize only the inputted eosinophil cell packing characteristics for the selected species to determine the eosinophil cell count information from the eosinophil cell band length data; and (g) display means for providing numerical indications of the eosinophil cell count information of the selected species of animal.

* * * * *